US006844000B2

United States Patent
Cassell et al.

(10) Patent No.: US 6,844,000 B2
(45) Date of Patent: Jan. 18, 2005

(54) **USE OF *PARAPOX* B2L PROTEIN TO TREAT CANCER AND MODIFY IMMUNE RESPONSES**

(75) Inventors: Delanie Cassell, San Anselmo, CA (US); Jeffrey S. Tepper, San Carlos, CA (US); Isa Samuels, Oakland, CA (US); Nathalie Dubois-Stringfellow, Berkeley, CA (US)

(73) Assignee: Bayer Pharmaceuticals Corporation, West Haven, CT (US)

( * ) Notice: Subject to any disclaimer, the term of this patent is extended or adjusted under 35 U.S.C. 154(b) by 0 days.

(21) Appl. No.: 10/313,332

(22) Filed: Dec. 6, 2002

(65) Prior Publication Data

US 2003/0109483 A1 Jun. 12, 2003

Related U.S. Application Data

(60) Provisional application No. 60/336,694, filed on Dec. 7, 2001.

(51) Int. Cl.[7] ........................ A61K 47/42; A61K 39/275
(52) U.S. Cl. ................................ 424/278.1; 424/281.1; 424/277.1; 424/232.1; 514/2; 514/12
(58) Field of Search ........................... 424/278.1, 281.1, 424/277.1, 232.1; 514/2, 18, 12, 44

(56) References Cited

U.S. PATENT DOCUMENTS

| 5,094,850 | A | | 3/1992 | Mayr et al. |
|---|---|---|---|---|
| 6,162,600 | A | * | 12/2000 | Mayr ............................. 435/5 |
| 6,316,007 | B1 | | 11/2001 | Nordquist et al. |
| 6,365,393 | B1 | | 4/2002 | Schmeer et al. |
| 6,406,699 | B1 | | 6/2002 | Wood |
| 6,406,705 | B1 | | 6/2002 | Davis et al. |
| 2002/0028195 | A1 | * | 3/2002 | Coffey et al. ............ 424/93.21 |
| 2002/0061298 | A1 | | 5/2002 | Coffey et al. |
| 2002/0076418 | A1 | | 6/2002 | Hirth-Dietrich et al. |
| 2002/0131979 | A1 | | 9/2002 | Hennessy et al. |
| 2003/0021769 | A1 | * | 1/2003 | Weber et al. ............ 424/93.21 |

FOREIGN PATENT DOCUMENTS

| EP | 0 669 133 | 8/1995 |
|---|---|---|
| WO | WO 95/22978 | 8/1995 |
| WO | WO 97/32029 | 9/1997 |
| WO | WO 97/37031 | 10/1997 |
| WO | WO 97/38724 | 10/1997 |
| WO | WO 00/69455 | 11/2000 |
| WO | WO 02/04002 | 1/2002 |

* cited by examiner

Primary Examiner—Mary E. Mosher
(74) Attorney, Agent, or Firm—John W. Mahoney

(57) ABSTRACT

A purified *Parapoxvirus ovis* envelope protein termed "B2L" can be used as a monotherapeutic agent. B2L protein also can be used in screening methods to identify potential therapeutic agents for modulating a subject's immune response to the B2L protein.

4 Claims, 9 Drawing Sheets

SEQUENCE LISTING

<160> NUMBER OF SEQ ID NOS: 4

<210> SEQ ID NO 1
<211> LENGTH: 378
<212> TYPE: PRT
<213> ORGANISM: Parapox ovis strain NZ2

<400> SEQUENCE: 1

Met Trp Pro Phe Ser Ser Ile Pro Leu Gly Ala Asp Cys Arg Val Val
1               5                   10                  15

Glu Thr Leu Pro Ala Glu Val Ala Ser Leu Ala Gln Gly Asn Met Ser
            20                  25                  30

Thr Leu Asp Cys Phe Thr Ala Ile Ala Glu Ser Ala Lys Lys Phe Leu
        35                  40                  45

Tyr Ile Cys Ser Phe Cys Cys Asn Leu Ser Ser Thr Lys Glu Gly Val
    50                  55                  60

Asp Val Lys Asp Lys Leu Cys Thr Leu Ala Lys Glu Gly Val Asp Val
65                  70                  75                  80

Thr Leu Leu Val Asp Val Gln Ser Lys Asp Lys Asp Ala Asp Glu Leu
                85                  90                  95

Arg Glu Ala Gly Val Asn Tyr Tyr Lys Val Lys Val Ser Thr Lys Glu
            100                 105                 110

Gly Val Gly Asn Leu Leu Gly Ser Phe Trp Leu Ser Asp Ala Gly His
        115                 120                 125

Trp Tyr Val Gly Ser Ala Ser Leu Thr Gly Gly Ser Val Ser Thr Ile
    130                 135                 140

Lys Asn Leu Gly Leu Tyr Ser Thr Asn Lys His Leu Ala Trp Asp Leu
145                 150                 155                 160

Met Asn Arg Tyr Asn Thr Phe Tyr Ser Met Ile Val Glu Pro Lys Val

-continued

```
                165                 170                 175

Pro Phe Thr Arg Leu Cys Cys Ala Ile Val Thr Pro Thr Ala Thr Asn
            180                 185                 190

Phe His Leu Asp His Ser Gly Gly Gly Val Phe Phe Ser Asp Ser Pro
        195                 200                 205

Glu Arg Phe Leu Gly Phe Tyr Arg Thr Leu Asp Glu Asp Leu Val Leu
    210                 215                 220

His Arg Ile Glu Asn Ala Lys Asn Ser Ile Asp Leu Ser Leu Leu Ser
225                 230                 235                 240
Met Val Pro Val Ile Lys His Ala Ser Ala Val Glu Tyr Trp Pro Gln
                245                 250                 255

Ile Ile Asp Ala Leu Leu Arg Ala Ala Ile Asn Arg Gly Val Arg Val
            260                 265                 270
Arg Val Ile Ile Thr Glu Trp Lys Asn Ala Asp Pro Leu Ser Val Ser
        275                 280                 285

Ala Ala Arg Ser Leu Asp Asp Phe Gly Val Gly Ser Val Asp Met Ser
    290                 295                 300

Val Arg Lys Phe Val Val Pro Gly Arg Asp Asp Ala Ala Asn Asn Thr
305                 310                 315                 320
Lys Leu Leu Ile Val Asp Asp Thr Phe Ala His Leu Thr Val Ala Asn
                325                 330                 335

Leu Asp Gly Thr His Tyr Arg Tyr His Ala Phe Val Ser Val Asn Ala
            340                 345                 350
Glu Lys Gly Asp Ile Val Lys Asp Leu Ser Ala Val Phe Glu Arg Asp
        355                 360                 365

Trp Arg Ser Glu Phe Cys Lys Pro Ile Asn
    370                 375

<210> SEQ ID NO 2
<211> LENGTH: 1557
<212> TYPE: DNA
<213> ORGANISM: Parapox ovis strain NZ2

<400> SEQUENCE: 2
ttaattttaa tttattggct tgcagaactc cgagcgccag tcccgctcga agaccgcgga     60
caggtccttg acgatgtcgc ccttctcggc gttcacgctc acgaaggcgt ggtagcggta    120
gtgcgtgccg tcgaggttgg cgaccgtgag gtgcgcgaag gtgtcgtcca cgatgagcag    180
cttagtgttg ttcgcggcgt cgtcccggcc gggtaccacg aacttgcgca cggacatgtc    240
cacgctgccg acgccaaagt cgtcgaggct gcgcgcggcc gagaccgaaa gcgggtccgc    300
gttcttccac tcggtaatga tcacgcgcac gcgcacgccg cggttgatgg ccgcgcgcag    360
cagcgcgtca atgatctgcg gccagtactc cacggcgctg gcgtgcttga tcaccggcac    420
catcgagagc agcgagaggt cgatgctgtt cttggcgttc tcgatgcggt gcagcacgag    480
gtcctcgtcg agcgtgcggt agaagcctag gaagcgctcc ggcgagtccg agaagaatac    540
gccgcccccg gagtggtcga ggtggaagtt cgtggccgtg ggcgtgacga tggcgcagca    600
gagccgcgtg aacggcacct tcggctccac gatcatggag tagaaggtgt tgtagcggtt    660
catgaggtcc caggccaggt gcttgttggt ggagtagagc ccgaggttct tgatggtgga    720
cacggacccg cccgtgagcg aggcgcttcc cacgtaccag tgcccggcgt ccgagagcca    780
gaagctgccg agaaggttgc cgacgccctc cttggtggac accttgacct tgtagtagtt    840
gacgcccgcc tcgcgcagct cgtccgcgtc cttgtccttg ctctgcacgt ccacgagcag    900
```

```
cgtgacgtct acgccctcct tggcgagcgt gcagagcttg tccttgacgt cgacgccctc     960
cttggtggag ctcaggttgc agcagaagct gcagatgtac aagaacttct tcgcggactc    1020
ggcgatagcg gtgaagcagt cgagggtgct catgttgccc tgcgccaaag acgccacctc    1080
tgcgggcagc gtctccacga cgcggcagtc ggcgcccagg gggatggagg agaacggcca    1140
catttattta tctcacaaaa ataatagggc ttcagggaaa gtcttttagc aggcgggcga    1200
gttcttcgag ttcgcttagg agttcttcca tttcttcgga agtcagcaac tggagctcgg    1260
acttgatttg aatatcttcg aggaaaccgt ctagcatgtt cgccatgtct ccggggagc     1320 actgcgccac atcttcgggg acaggatcgg gtgtgggcat taggtctccg cttacttgaa    1380
cgtcgtccat catcctgtcg atgaggtctt cgacttctag acggggtccg tagatcagca    1440
tatttggtga tggaggtagt ttaaggtgcg agagttagtg ttatacgacc gccaacgtgt    1500
gtttatcgcg cgtacatttt caataattaa caaactcccc ttcctgcgcc tgctcga      1557
```

<210> SEQ ID NO 3
<211> LENGTH: 378
<212> TYPE: PRT
<213> ORGANISM: Parapox ovis strain D1701

<400> SEQUENCE: 3

```
Met Trp Pro Phe Ser Ser Ile Pro Val Gly Ala Asp Cys Arg Val Val
1               5                   10                  15

Glu Thr Leu Pro Ala Glu Val Ala Ser Leu Ala Gln Gly Asn Met Ser
            20                  25                  30

Thr Leu Asp Cys Phe Thr Ala Ile Ala Glu Ser Ala Lys Lys Phe Leu
        35                  40                  45

Tyr Ile Cys Ser Phe Cys Cys Asn Leu Ser Ser Thr Lys Glu Gly Val
    50                  55                  60

Asp Val Lys Asp Lys Leu Cys Thr Leu Ala Lys Glu Gly Val Asp Val
65                  70                  75                  80

Thr Leu Leu Val Asp Val Gln Ser Lys Asp Lys Asp Ala Asp Glu Leu
                85                  90                  95

Arg Ala Ala Gly Val Asn Tyr Tyr Lys Val Lys Val Ser Thr Arg Glu
            100                 105                 110

Gly Val Gly Asn Leu Leu Gly Ser Phe Trp Leu Ser Asp Ala Gly His
        115                 120                 125

Trp Tyr Val Gly Ser Ala Ser Leu Thr Gly Gly Ser Val Ser Thr Ile
    130                 135                 140

Lys Asn Leu Gly Leu Tyr Ser Thr Asn Lys His Leu Ala Trp Gly Leu
145                 150                 155                 160

Met Asn Arg Tyr Asn Thr Phe Tyr Ser Met Ile Val Glu Pro Lys Val
                165                 170                 175

Pro Phe Thr Arg Leu Cys Cys Ala Val Val Thr Pro Thr Ala Thr Asn
            180                 185                 190

Phe His Leu Asn His Ser Gly Gly Gly Val Phe Phe Ser Asp Ser Pro
        195                 200                 205

Glu Arg Phe Leu Gly Phe Tyr Arg Thr Leu Asp Glu Asp Leu Val Leu
    210                 215                 220
```

-continued

His Arg Ile Glu Asn Ala Lys Asn Ser Ile Asp Leu Ser Leu Leu Ser
225 230 235 240

Met Val Pro Val Ile Lys His Ala Gly Ala Val Glu Tyr Trp Pro Arg
245 250 255

Ile Ile Asp Ala Leu Leu Arg Val Ala Ile Asn Arg Gly Val Arg Val
260 265 270

Arg Val Ile Ile Thr Glu Trp Lys Asn Ala Asp Pro Leu Ser Val Ser
275 280 285

Ala Ala Arg Ser Leu Asp Asp Phe Gly Val Gly Ser Val Asp Met Ser
290 295 300

Val Arg Lys Phe Val Val Pro Gly Arg Asp Asp Ala Ala Asn Asn Thr
305 310 315 320

Lys Leu Leu Ile Val Asp Asp Thr Phe Ala His Leu Thr Val Ala Asn
325 330 335

Leu Asp Gly Thr His Tyr Arg Tyr His Ala Phe Val Ser Val Asn Ala
340 345 350

Glu Lys Gly Asp Ile Val Lys Asp Leu Ser Ala Val Phe Glu Arg Asp
355 360 365

Trp Arg Ser Glu Phe Cys Lys Pro Ile Asn
370 375

<210> SEQ ID NO 4
<211> LENGTH: 1136
<212> TYPE: DNA
<213> ORGANISM: Parapox ovis strain D1701

<400> SEQUENCE: 4
atgtggccgt tctcctccat ccccgtgggc gccgactgcc gcgtcgtgga gacgctgccc 60
gcagaggtgg cgtccctggc gcagggcaac atgagcaccc tcgactgctt caccgccatc 120
gccgagtccg cgaagaagtt tttgtacatc tgcagcttct gctgcaacct gagctccacc 180
aaggagggcg tcgacgtcaa agacaagctc tgcacgctcg ccaaggaggg cgttgacgtc 240
acgctgctcg tggacgtgca gagcaaggac aaggacgcgg acgagctgcg cgcggcgggc 300
gtcaactact acaaggtcaa ggtgtccacg cgggaaggcg tcggcaacct tctcggcagc 360
ttctggctct cggacgccgg gcactggtac gtgggcagcg cctcgctcac gggcgggtcc 420
gtgtccacca tcaagaacct cgggctctac tccaccaaca agcacctggc ctggggcctc 480
atgaaccgct acaacacctt ctactccatg atcgtggagc cgaaggtgcc gttcacgcgg 540
ctctgctgcg ccgtcgtcac gcccacggcc acgaacttcc acctcaacca ctccgggggc 600
ggcgtattct tctcggactc gccggagcgc ttcctaggct tctaccgcac gctcgacgag 660
gacctcgtgc tgcaccgcat cgagaacgcc aagaacagca tcgacctctc gctgctctcg 720
atggtgccgg tgatcaagca cgccggcgcc gtggagtact ggccgcggat catagacgcg 780
ctgctgcgcg tggccatcaa ccgcggcgtg cgcgtgcgcg tgatcatcac cgagtggaag 840
aacgcggacc cgctgtcggt ctcggccgcg cgcagcctcg acgactttgg cgtcggtagc 900
gtggacatgt ccgtgcgcaa gttcgtggta cccggccggg acgacgctgc gaacaacacc 960
aagctgctta tcgtggacga caccttcgcg cacctcacgg tcgccaacct cgacggcacg 1020
cactaccgct accacgcctt cgtgagcgtg aacgccgaga agggcgacat cgtcaaggac 1080
ctgtccgcgg tcttcgagcg ggactggcgc tcggagttct gcaagccaat aaataa 1136

USE OF *PARAPOX* B2L PROTEIN TO TREAT CANCER AND MODIFY IMMUNE RESPONSES

This application claims the benefit of and incorporates by reference now abandoned provisional application Ser. No. 60/336,694 filed Dec. 7, 2001.

FIELD OF THE INVENTION

The invention relates to the field of cancer therapy and immunotherapy. More particularly, the invention relates to the use of a purified B2L viral envelope protein of a *Parapox* virus as a therapeutic agent. The invention also relates to screening methods to identify potential therapeutic agents that modify the effect of B2L protein.

BACKGROUND OF THE INVENTION

Attenuated *Parapox* viruses can be used to induce *Parapox*-specific immunity. U.S. Pat. No. 6,162,600. In addition, the highly attenuated strain D1701 (Baypamun HK®) is used as a non-specific immunomodulator (Buttner et al., *Immunol. Microbiol. Infect. Dis.* 16, 1–10, 1993) to promote immunity to heterologous pathogens. The virus also infects humans and induces nonspecific production of immune modulating cytokines in cultures of human PBMC (Buttner et al., *Vet. Immunol. Immunopathol.* 46, 237–50, 1995).

Attenuation of *Parapoxvirus ovis*, however, is time-consuming, taking from 100 to 200 culture passages; according to WO 95/22978, it takes from three to five years to perform each 100 passages, depending on the species of virus used. Attenuation can, therefore, "encompass a period lasting from ten to twenty years." (See WO 95/22978, page 9).

WO 95/22978 discloses the use of combinations of two or more individual *Parapox* virus components as "multipotent paramunity inducers" for use as adjuvant therapy for tumors and the prevention of metastases. The components can be individual polypeptides or detached envelopes of poxviruses. WO 95/22978, however, does not disclose any particular viral polypeptides other than the viral fusion protein and adsorption protein. Moreover, WO 95/22978 teaches that the disclosed paramunity inducers have virtually no immunogenic properties. There is a need in the art for simple, effective therapeutic agents that can be used to enhance immune responses and to treat infectious diseases and cell proliferative disorders, including tumors and dysplastic lesions.

SUMMARY OF THE INVENTION

It is an object of the invention to provide reagents and methods for modifying immune responses to endogenous (nonadministered) antigens. This and other objects of the invention are provided by one or more of the embodiments described below.

It is an object of the invention to provide a method of enhancing an immune response to endogenous antigens, comprising the steps of administering to a subject in need thereof an effective amount of a B2L viral envelope protein of a *Parapox* virus, whereby the B2L viral envelope protein enhances the immune response to endogenous antigens.

It is an object of the invention to provide a method of eliciting an immune response to B2L protein, comprising the steps of administering to a subject in need thereof an effective amount of a B2L viral envelope protein of a *Parapox* virus, whereby an immune or inflammatory response to the B2L viral envelope protein is generated.

Another embodiment of the invention provides a method of enhancing an immune response to endogenous antigens comprising the steps of administering to a mammal or more specifically a human in need thereof an effective amount of a B2L viral envelope protein of a *Parapox* virus wherein the B2L protein is administered to the subject by means of a nucleotide encoding the B2L protein.

Another embodiment of the invention provides a method of enhancing an immune response to endogenous antigens comprising the steps of administering to a mammal or more specifically a human in need thereof an effective amount of a B2L viral envelope protein of a *Parapox* virus, wherein the *Parapox* virus is *Parapoxvirus ovis*, or more specifically a *Parapoxvirus ovis* strain selected from the group consisting of NZ2, NZ7, NZ10, and D1701.

Another embodiment of the invention provides a method of enhancing an immune response to endogenous antigens, comprising the steps of administering to a subject in need thereof an effective amount of a B2L viral envelope protein of a *Parapox* virus, whereby the B2L viral envelope protein enhances the immune response to endogenous antigens, wherein the endogenous antigens are associated with a cell proliferative disorder or an infectious pathogen.

Another embodiment of the invention provides a method of enhancing an immune response to endogenous antigens, comprises the steps of administering intradermally, subcutaneously, intratumorally, or intravenously to a subject in need thereof an effective amount of a B2L viral envelope protein of a *Parapox* virus.

In yet another embodiment of the invention, a method is provided for treating a patient having a cell proliferative disorder, comprising the step of administering to the patient an effective amount of a B2L viral envelope protein of a *Parapox* virus, whereby symptoms of the patient's cell proliferative disorder are ameliorated.

In yet another embodiment of the invention, a method is provided for treating a patient having a cell proliferative disorder, comprising the step of administering systemically or by injection into a tumor or dysplastic lesion of a patient an effective amount of a B2L viral envelope protein of a *Parapox* virus, whereby symptoms of the patient's cell proliferative disorder are ameliorated.

In yet another embodiment of the invention, a pharmaceutical composition is provided that comprises a B2L viral envelope protein of a *Parapox* virus.

In yet another embodiment of the invention, a pharmaceutical composition is provided that comprises a B2L viral envelope protein a *Parapoxvirus ovis* strain selected from the group consisting of NZ2, NZ7, NZ10, and D1701.

In yet another embodiment of the invention, a method is provided for identifying test compounds with the ability to modify a subject's immune and/or inflammatory response to B2L protein, comprising the steps of: contacting a dendritic cell in vitro with a sufficient amount of a purified B2L protein to observe a chemotactic effect of the B2L protein on the dendritic cell; and contacting the dendritic cell with the test compound, whereby a test compound that enhances the chemotactic effect of the B2L protein on the dendritic cell is identified as a potential agent for enhancing the subject's immune response to the B2L protein and whereby a test compound that decreases the chemotactic effect of the B2L protein on the dendritic cell is identified as a potential agent for inhibiting the subject's immune response to the B2L protein.

In yet another embodiment of the invention, a method is provided for identifying test compounds with the ability to modify a subject's immune and/or inflammatory response to B2L protein, comprising the steps of simultaneously contacting a dendritic cell in vitro with a sufficient amount of a purified B2L protein and a test compound to observe a chemotactic effect of the B2L protein and test compound on the dendritic cell to identify as a potential agent for enhancing the subject's immune response to the B2L protein.

In still another embodiment of the invention, a method is provided for identifying a test compound with the ability to modify a subject's immune response to a B2L protein, comprising the steps of contacting a purified B2L protein in vitro with a test compound; and determining whether the test compound and the B2L protein form a complex, whereby a test compound that forms a complex with the B2L protein is identified as a potential agent for modifying the subject's immune response to the B2L protein.

In yet another embodiment of the invention, a method is provided for identifying test compounds with the ability to modify a subject's immune and/or inflammatory response to B2L protein, comprising the steps of contacting a peripheral blood mononuclear cell in vitro with a sufficient amount of a purified B2L protein to observe a cytokine-inducing effect of the B2L protein on the peripheral blood mononuclear cells, whereby a test compound that enhances the cytokine-inducing effect of the B2L protein on the mononuclear cell is identified as a potential agent for enhancing the subject's immune response to the B2L protein and whereby a test compound that decreases the cytokine-inducing effect of the B2L protein on the mononuclear cell is identified as a potential agent for inhibiting the subject's immune response to the B2L protein.

Thus, the invention provides pharmaceutical compositions and methods for using B2L protein as a monotherapeutic agent, as well as methods of using B2L protein to identify agents that can modify the effects of B2L protein.

DETAILED DESCRIPTION OF THE INVENTION

Figure 1:
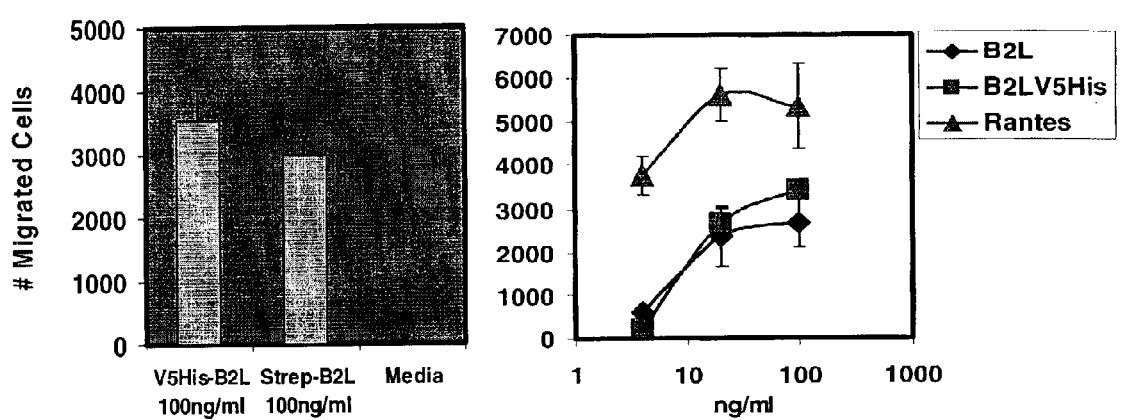
FIG. 1. Chemotactic effect of B2L protein on human dendritic cell-enriched cultures of peripheral blood mononuclear cells.
Figure 3:
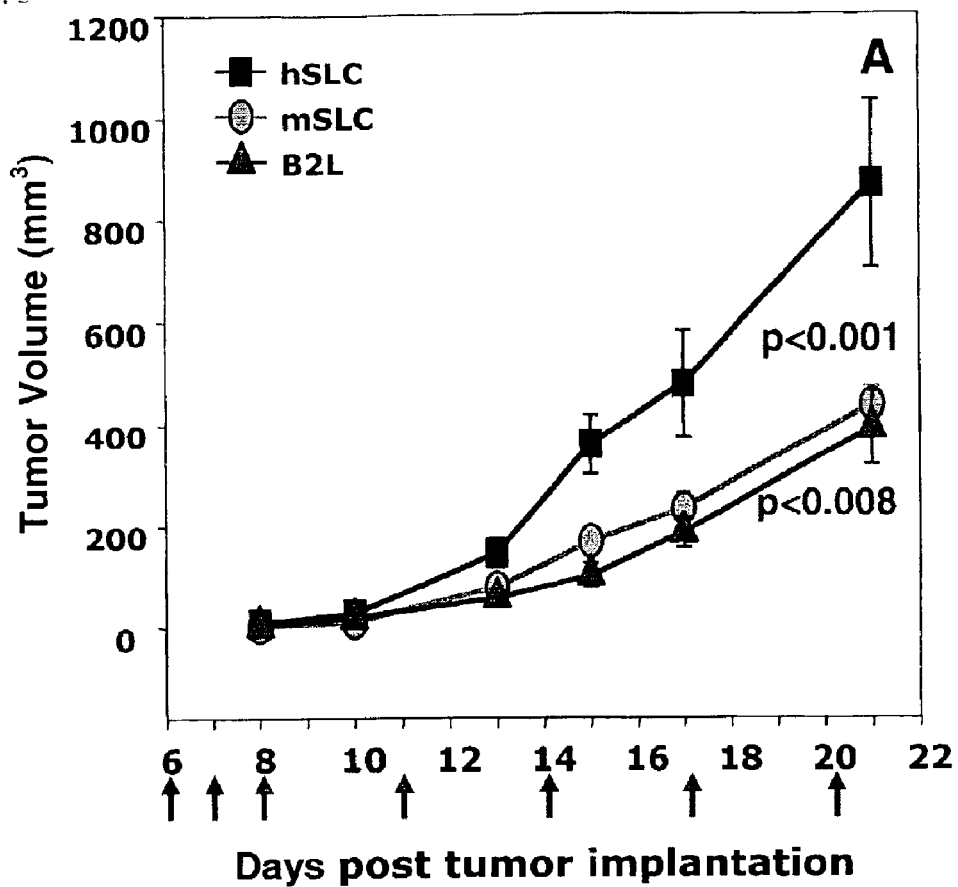
FIG. 3. Local and systemic anti-tumor effect of intratumorally administered B2L protein.
Figure 3:
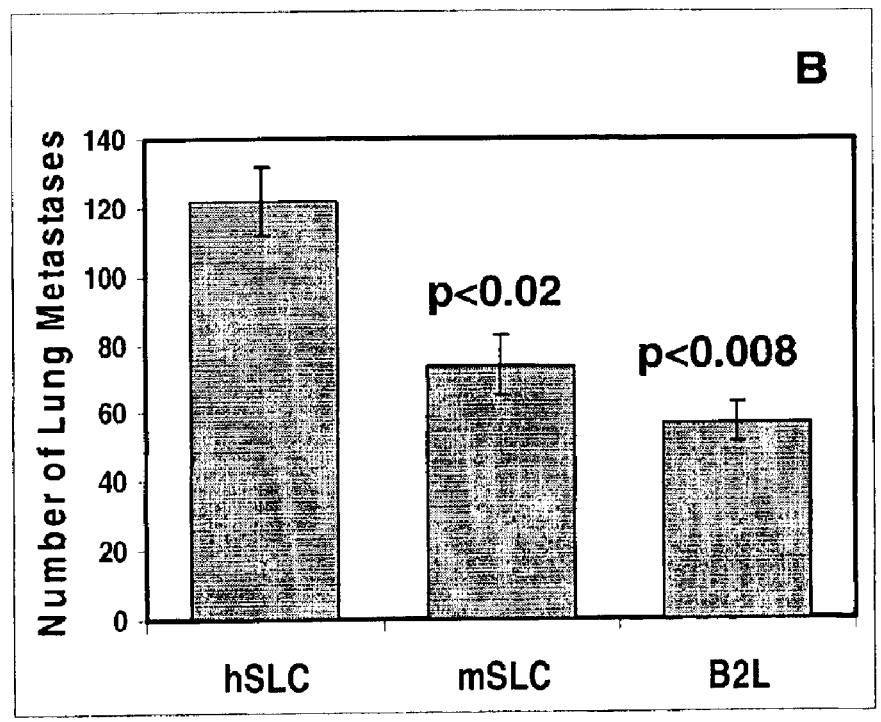
Figure 4:
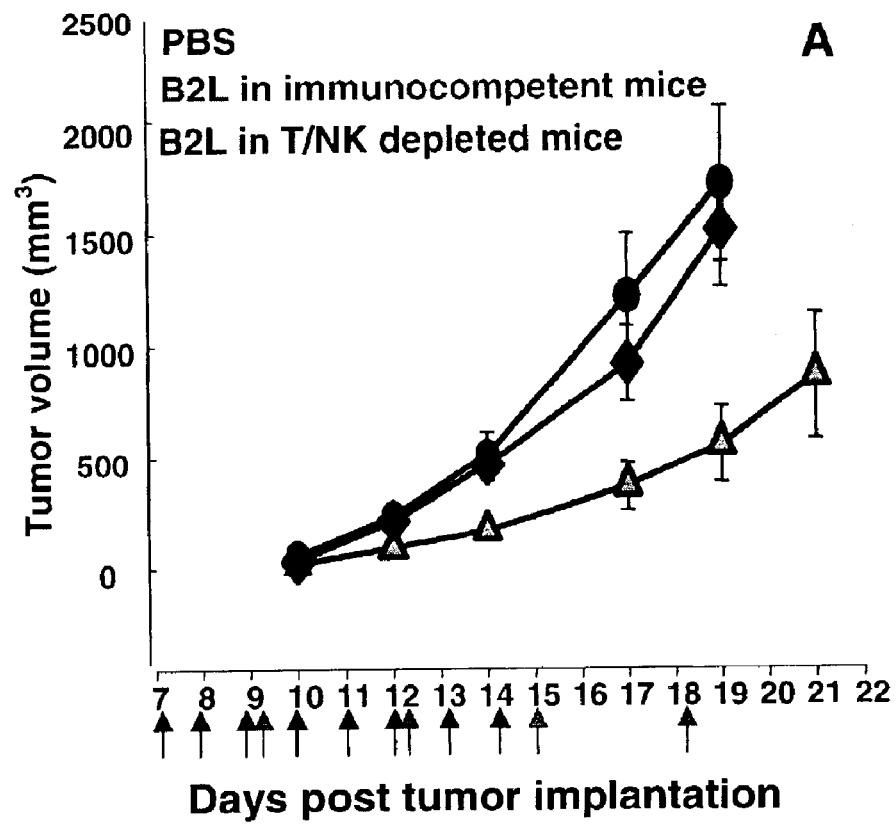
FIG. 4. Immune dependence of local and systemic anti-tumor effect of intratumorally administered B2L protein.
Figure 4:
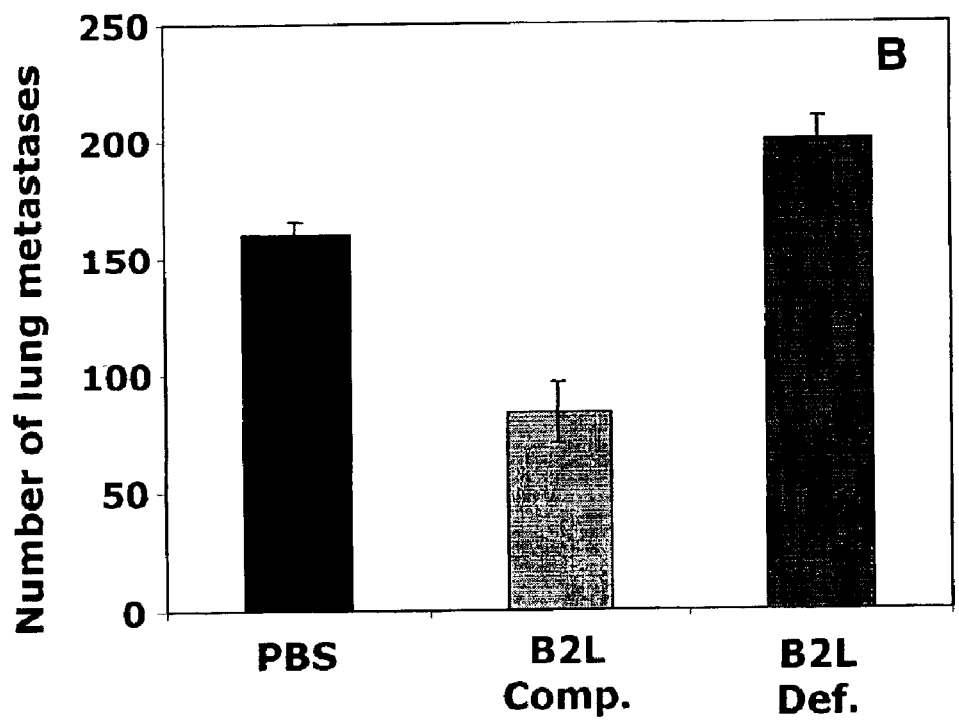

The invention is based on the ability of a *Parapox* viral envelope protein termed "B2L" to enhance a subject's immune response to endogenous (nonadministered) antigens. B2L is the second open reading frame in the BamHI B fragment of the Orf virus genome. Sullivan et al., *Virology* 202, 968–73, 1994. B2L is an immunogenic protein; in fact, B2L protein is the dominant focus of the antibody response mounted in infected sheep. Sullivan et al., 1994. The prior art teaches that, as the activity of epitopes responsible for antigen-specific immunization decrease, nonspecific immunostimulatory activity of the preparations increases. See WO 95/22978, page 4. Thus, immunogenicity of B2L does not predict its ability to modulate immune responses to endogenous antigens. While not wishing to be bound by any particular hypothesis, we believe that B2L, like chemokines, recruits dendritic cells to the site of administration and induces immunity. The ability of B2L to recruit dendritic cells to the injection site promotes activation of helper T cells and cytotoxic T lymphocytes specific for endogenous antigens expressed at the site. In support of this hypothesis, purified B2L protein from mammalian cells transfected with B2L is chemotactic in vitro for human dendritic cell-enriched populations (Example 1 and FIG. 1). Purified B2L protein also exhibits chemotactic activity on murine dendritic cell-enriched cultures with a potency greater than or equal to that observed with secondary lymphoid chemokine (SLC), a chemokine reported to recruit dendritic cells in vitro and in vivo (Example 2 and FIG. 2). Upon intratumoral injection, purified B2L protein inhibits tumor growth (Example 3 and FIG. 3) in an immune dependent fashion (Example 4 and FIG. 4).

Figure 5:
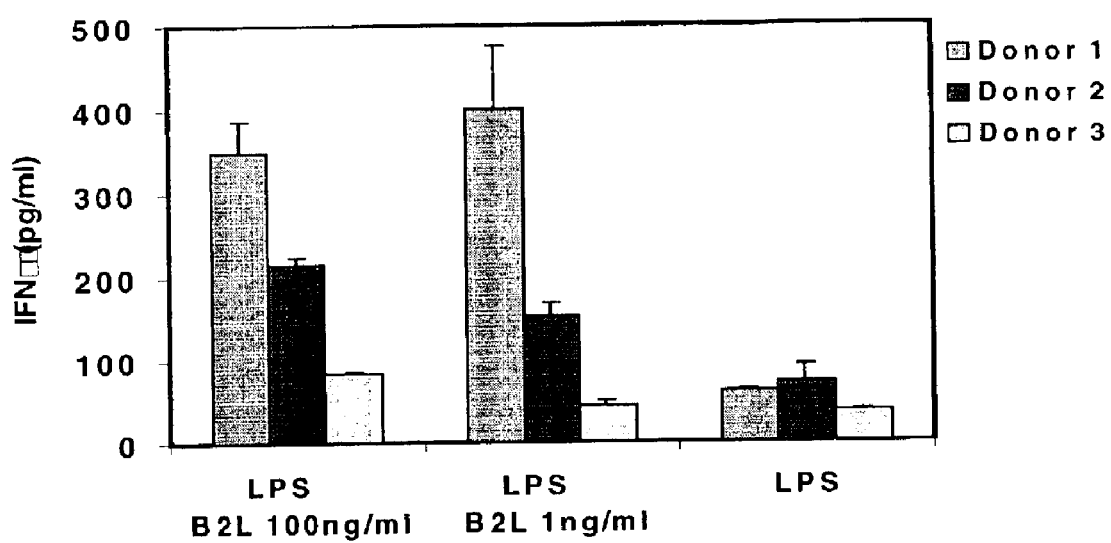
FIG. 5. B2L augments IFNγ production by human PBMC

As has been suggested for other dendritic cell chemotaxins, the chemotactic function of B2L suggests that organization of a local immunologic microenvironment plays a role in its immunostimulatory mechanism of action. Conversely, systemic administration would not be expected to lead to such local organization and, if that were the sole activity of B2L, would not be expected to exhibit antitumor activity. The parent virus has been demonstrated to elicit nonspecific immunostimulatory effects, believed to be cytokine mediated, when administered systemically. Since the virus expresses multiple immunologically relevant proteins, it was not clear which proteins might account for the systemic effect. To our knowledge, activities beyond dendritic cell recruitment and its immunologic consequences have not been demonstrated for B2L prior to the studies described herein. These studies demonstrate that B2L augments production by human PBMC of IFNγ (Example 5 and FIG. 5), a cytokine with known antitumor activity and exhibits robust antitumor activity when administered systemically (Examples 6, 7, 8 and FIGS. 6, 7, 8). While not wishing to be bound by any particular hypothesis, we believe that B2L, like its parent virus, nonspecifically stimulates production of IFNγ when administered systemically. IFNγ may both promote development of an antitumor immune response by facilitating the generation of cytotoxic effector cells, by increasing the expression of major histocompatability complex (MHC) antigens on tumors, rendering them more susceptible to being destroyed by cytotoxic effector cells, and by facilitating the generation of tumor-specific antibodies.

Treatment with the highly attenuated parent virus promotes immunity to heterologous pathogens, an effect believed to depend on the induction of multiple cytokines. While not wishing to be bound by any particular hypothesis, we believe that B2L, like its parent virus, nonspecifically stimulates production of multiple cytokines when administered systemically. Therefore, treatment with the B2L protein may similarly promote immunity to heterologous pathogen.

B2L Proteins

B2L proteins for use in the compositions and methods described herein are those of the *Parapoxvirus* genus, such as Orf virus (OV), particularly the *Parapoxvirus ovis* strains NZ2, NZ7, NZ10, and D1701. Orf viruses are reviewed in Robinson & Balassu, *Vet. Bull.* 51, 771, 1981; Robinson & Lyttle, in Binns & Smith, eds., Recombinant Poxviruses, Chapter 9, pp. 306–17, CRC Press, Boca Raton, 1992. An amino acid sequence for the B2L protein of OV NZ2 is disclosed in Sullivan et al., Identification and characterization of an orf virus homologue of the vaccinia virus gene encoding the major envelope antigen p37K, *Virology* 202 (2), 968–73, 1994, and is shown in SEQ ID NO:1. A coding sequence for SEQ ID NO:1 is shown in SEQ ID NO:2. The amino acid sequences of the B2L proteins obtained from D1701 and NZ2 are highly conserved. The amino acid sequence of the D1701 protein is shown in SEQ ID NO: 3. A coding sequence for SEQ ID NO: 3 is shown in SEQ ID NO: 4.

Purified B2L protein is separated from other compounds that normally associate with the B2L protein in the virus, such as other envelope components. A preparation of purified B2L protein is at least 80% pure; preferably, the preparations are 90%, 95%, or 99% pure. Purity of the preparations can be assessed by any means known in the art, such as SDS-polyacrylamide gel electrophoresis.

Purified B2L protein for use in compositions and methods of the invention can be purified from *Parapox* viruses or from cells infected by the viruses, by recombinant DNA methods, and by chemical synthesis. Purification methods include, but are not limited to, size exclusion chromatography, ammonium sulfate fractionation, ion exchange chromatography, affinity chromatography, and preparative gel electrophoresis.

B2L protein can be expressed recombinantly, after insertion of B2L coding sequences into an expression vector that contains the necessary elements for the transcription and translation of the inserted coding sequence. Maintenance of orf viruses in culture is disclosed in WO 97/37031. A preferred system for maintaining and expressing B2L protein is HKB11 cells transfected with B2L in a vector such as a p2ToP, pCEP4, or pcDNA3.1 vector (Invitrogen). Recombinantly produced B2L protein can be secreted into the culture medium and purified. Methods for producing proteins recombinantly are well known to those skilled in the art.

A B2L protein also can be produced using chemical methods to synthesize its amino acid sequence, such as by direct peptide synthesis using solid-phase techniques (Merrifield, *J. Am. Chem. Soc.* 85, 2149–2154, 1963; Roberge et al., *Science* 269, 202–204, 1995). Protein synthesis can be performed using manual techniques or by automation. Optionally, fragments of a B2L protein can be separately synthesized and combined using chemical methods to produce a full-length molecule.

"B2L protein" as used herein includes both functional portions of B2L and full-length or partial biologically active B2L variants. Biologically active variants comprise amino acid substitutions, insertions, and/or deletions with respect to the amino acid sequence shown in SEQ ID NO:1. Amino acid substitutions are defined as one for one amino acid replacements. They are conservative in nature when the substituted amino acid has similar structural and/or chemical properties. Examples of conservative replacements are substitution of a leucine with an isoleucine or valine, an aspartate with a glutamate, or a threonine with a serine.

Amino acid insertions or deletions are changes to or within an amino acid sequence. They typically fall in the range of about 1 to 5 amino acids. Guidance in determining which amino acid residues can be substituted, inserted, or deleted without abolishing biological or immunological activity of a B2L protein can be found using computer programs well known in the art, such as DNASTAR software. Biological activity of a B2L protein having an amino acid substitution, insertion, and/or deletion can be tested, for example, using the in vitro assays described in Examples 1 and 2.

Functional portions of B2L comprising, for example, 25, 50, 75, 100, 125, 150, 175, 200, 225, 250, 275, 300, 325, 350, 360, 370, 375, or 377 amino acids, also can be used in the compositions and methods of the invention, provided that the portions of B2L retain biological activity, e.g., the ability to enhance an immune response and/or exert a chemotactic effect on enriched dendritic cell populations and/or exert a cytokine-inducing effect on peripheral blood mononuclear cells.

Pharmaceutical Compositions

Purified B2L protein can be used in pharmaceutical compositions. Pharmaceutical compositions of the invention can be used to produce tumor and pathogen protection in mammals, including laboratory animals (e.g., mice, rats, hamsters, guinea pigs), companion animals (e.g., dogs, cats), farm animals (e.g., horses, cows, sheep, pigs, goats), and humans.

Pharmaceutical compositions of the invention include a pharmaceutically acceptable carrier. Typically these will be sterile formulations in a diluent or vehicle which is free of pyrogenic components. Buffers, stabilizers, and the like can be included, as is known in the art. Optionally, pharmaceutical compositions include conventional adjuvants, such as aluminum hydroxide and aluminum phosphate (collectively commonly referred to as alum), saponins complexed to membrane protein antigens (immune stimulating complexes), pluronic polymers with mineral oil, killed mycobacteria in mineral oil, Freund's complete adjuvant, bacterial products, such as muramyl dipeptide, and lipopolysaccharides.

B2L-containing compositions can be administered alone or can be co-administered with one or more other therapeutic agents, such as a tumor-specific antibody or cytokine. "Co-administration" includes administration of B2L and another therapeutic agent separately or in the same composition.

A large number of antibodies have been described which are specifically reactive with tumor-associated antigens. Many are available from the American Type Culture Collection, 10801 University Blvd., Manassas, Va. 20110–2209, including those to breast, lung, and melanoma tumor cells. For a review of tumor-specific antibodies see Foon, *Cancer Research* 49, 1621–31, 1989.

Endogenous, nonadministered antigens comprise tumor antigens and/or those produced by natural infection with a pathogen. Antigens include any component that is recognized by cells of the immune system. Endogenous tumor antigens include, but are not limited to, α-fetoprotein, BAGE, β-HCG, CEA, ESO, GAGE, gangliosides, Her-2/neu, HPV E6/E7, immunoglobulins, MAGE-1, MAGE-2, MAGE-3, MAGE-4, MAGE-12, MART-1, Melan-A, melanoma antigen gp75, gp100, MN/G250, MUC1, MUC2, MUC3, MUC4, MUC18, PSA, PSM, RAGE, ras, SART-1, telomerase, thyroperoxidases, tyrosinases, and p53. Endogenous pathogen-associated antigens include, but are not limited to, those produced by natural infection with human immunodeficiency viruses, Herpes viruses, hepatitis viruses, pox viruses, flu viruses, measles, mumps, rubella, rabies, respiratory syncytial viruses, *Bacillus anthracis, Bordetella pertussis, Borrelia burgdorferi, Clostridium tetani, Corynebacterium diphtheriae, Haemophilus influenza B, Neisseria meningitidis, Salmonella typhi, Streptococcus pneumoniae,* and *Vibrio cholerae.*

Routes of administration include, without limitation, subcutaneous, intravenous, nasal, ophthalmic, transdermal, intramuscular, intradermal, intragastric, perlingual, alveolar, gingival, intraperitoneal, intravaginal, pulmonary, rectal, and oral administration. Administration can be by any suitable means, including injection, topical administration, ingestion, or inhalation. Single and/or multiple administrations are contemplated.

Optionally, B2L protein can be administered using a nucleotide (DNA or RNA) molecule encoding the protein. Use of DNA-encoded elicitors of immune responses is discussed, for example, in McDonnel & Askari, *New Engl. J. Med.* 334, 42–45, 1996; Robinson, *Can. Med. Assoc. J.* 152, 1629–32, 1995; Fynan et al., *Int. J. Immunopharmacol.* 17, 79–83, 1995; Pardoll & Beckerleg, *Immunity* 3, 165–69, 1995, and Spooner et al., *Gene Therapy* 2, 173–80, 1995.

Dosage

The determination of a therapeutically effective dose of B2L is well within the capability of those skilled in the art. A therapeutically effective dose refers to that amount of active ingredient (i.e., B2L protein or nucleic acid encoding B2L) that results in an augmentation of the immune response to cancer or an endogenous antigen over that which occurs in the absence of the therapeutically effective dose.

The therapeutically effective dose can be estimated initially either in cell culture assays or in animal models, usually mice, rats, rabbits, dogs, or pigs. The animal model also can be used to determine the appropriate concentration range and route of administration. Such information can then be used to determine useful doses and routes for administration in humans.

Therapeutic efficacy and toxicity, e.g., $ED_{50}$ (the dose therapeutically effective in 50% of the population) and $LD_{50}$ (the dose lethal to 50% of the population), can be determined by standard pharmaceutical procedures in cell cultures or experimental animals. The dose ratio of toxic to therapeutic effects is the therapeutic index, and it can be expressed as the ratio, $LD_{50}/ED_{50}$.

Pharmaceutical compositions that exhibit large therapeutic indices are preferred. The data obtained from cell culture assays and animal studies is used in formulating a range of dosage for human use. The dosage contained in such compositions is preferably within a range of circulating concentrations that include the $ED_{50}$ with little or no toxicity. The dosage varies within this range depending upon the dosage form employed, sensitivity of the patient, and the route of administration.

Suitable dosages and treatment regimens for administration of either B2L protein or nucleic acid molecules encoding B2L include, but are not limited to, daily, twice- or three-times weekly, weekly, bi-weekly, monthly, bimonthly, or yearly treatments of about 1, 5, 10, 15, 20, 25, 50, 75, 100, or 200 $\mu g/m^2$ (or approximately 0.05, 0.1, 0.2, 0.25, 0.3, 0.5, 0.75, 1, 2, 5, or 10 mg/kg). Preferred routes of administration include subcutaneous, intradermal, intramuscular administration. The exact dosage, treatment regimen, and route of administration, however, will be determined by the practitioner, in light of factors related to the subject that requires treatment.

Treatment of Cell Proliferative Disorders

In one embodiment, the invention provides a therapeutic agent for cell proliferative disorders. A "cell proliferative disorder" includes both benign and malignant cell populations that differ morphologically from the surrounding tissue. A cell proliferative disorder as described herein may be a neoplasm. A neoplasm is a new, abnormal growth of cells or a growth of abnormal cells that reproduce faster than normal. A neoplasm can create an unstructured mass (a tumor), which can be either benign or malignant. For example, the neoplasm may be a brain, head, neck, skin, lung, esophageal, stomach, small bowel, colon, bladder, kidney, or cervical neoplasm. A benign tumor is a tumor that is noncancerous, e.g., its cells do not proliferate or invade surrounding tissues. A malignant tumor comprises cells that may become metastatic. A neoplasm also includes an abnormal proliferation of blood cells such as occurs in leukemias, lymphomas, polycythemia vera, thrombocytosis, and the like.

Cell proliferative disorders also include disorders such as anhydric hereditary ectodermal dysplasia, congenital alveolar dysplasia, epithelial dysplasia of the cervix, fibrous dysplasia of bone, and mammary dysplasia. Cell proliferative disorders also include hyperplasias, for example, endometrial, adrenal, breast, prostate, thyroid hyperplasias, and pseudoepitheliomatous hyperplasia of the skin.

For treatment of neoplasms or other cell proliferative lesions, pharmaceutical compositions of the invention preferably are administered by injection. For example, B2L protein itself can be injected directly into the abnormal tissue or into the surrounding tissue, although other means of administration can be used. If desired, conjugates of B2L protein with, e.g., a tumor-specific antibody, preferably are administered systemically.

Screening Methods

The invention also provides methods of screening test compounds to identify those which are potential agents for modulating an immune response, particularly an individual's immune response to B2L.

Test compounds can be pharmacologic agents already known in the art or can be compounds previously unknown to have any pharmacological activity. The compounds can be naturally occurring or designed in the laboratory. They can be isolated from microorganisms, animals, or plants, and can be produced recombinantly, or synthesized by chemical methods known in the art. If desired, test compounds can be obtained using any of the numerous combinatorial library methods known in the art, including but not limited to, biological libraries, spatially addressable parallel solid phase or solution phase libraries, synthetic library methods requiring deconvolution, the "one-bead one-compound" library method, and synthetic library methods using affinity chromatography selection.

Methods for the synthesis of molecular libraries are well known in the art (see, for example, DeWitt et al., *Proc. Natl. Acad. Sci. U.S.A.* 90, 6909, 1993; Erb et al. *Proc. Natl. Acad. Sci. U.S.A.* 91, 11422, 1994; Zuckermann et al., *J. Med. Chem.* 37, 2678, 1994; Cho et al., *Science* 261, 1303, 1993; Carell et al., *Angew. Chem. Int. Ed. Engl.* 33, 2059, 1994; Carell et al., *Angew. Chem. Int. Ed. Engl.* 33, 2061; Gallop et al., *J. Med. Chem.* 37, 1233, 1994). Libraries of compounds can be presented in solution (see, e.g., Houghten, BioTechniques 13, 412–421, 1992), or on beads (Lam, Nature 354, 82–84, 1991), chips (Fodor, Nature 364, 555–556, 1993), bacteria or spores (Ladner, U.S. Pat. No. 5,223,409), plasmids (Cull et al., Proc. Natl. Acad. Sci. U.S.A. 89, 1865–1869, 1992), or phage (Scott & Smith, Science 249, 386–390, 1990; Devlin, Science 249, 404–406, 1990; Cwirla et al., Proc. Natl. Acad. Sci. 97, 6378–6382, 1990; Felici, J. Mol. Biol. 222, 301–310, 1991; and Ladner, U.S. Pat. No. 5,223,409).

Screening assays of the invention can employ test compounds together with in chemotaxis assays, such as those disclosed in Examples 1 and 2 or in cytokine induction assays, such as that disclosed in Example 5. Alternatively, purified B2L protein can be contacted with test compounds in vitro and the formation of a complex between B2L and the test compound determined. Optionally, either the B2L protein or the test compound can comprise a detectable label, such as a fluorescent, radioisotopic, chemiluminescent, or enzymatic label, to facilitate detection of B2L-test compound complexes.

Any means known in the art can be used to determine whether a B2L-test compound complex has been formed. Such methods include, without limitation, yeast two-hybrid assays (e.g., U.S. Pat. No. 5,283,317; Zervos et al., Cell 72, 223–232, 1993; Madura et al., J. Biol. Chem. 268, 12046–12054, 1993; Bartel et al., BioTechniques 14, 920–924, 1993; Iwabuchi et al., Oncogene 8, 1693–1696, 1993; and Brent W094/10300), real-time Bimolecular Interaction Analysis (BIA) (Sjolander & Urbaniczky, Anal. Chem. 63, 2338–2345, 1991, and Szabo et al., Curr. Opin. Struct. Biol. 5, 699–705, 1995), and detection of complexes via non-denaturing SDS polyacrylamide gel electrophoresis.

Figure 2:
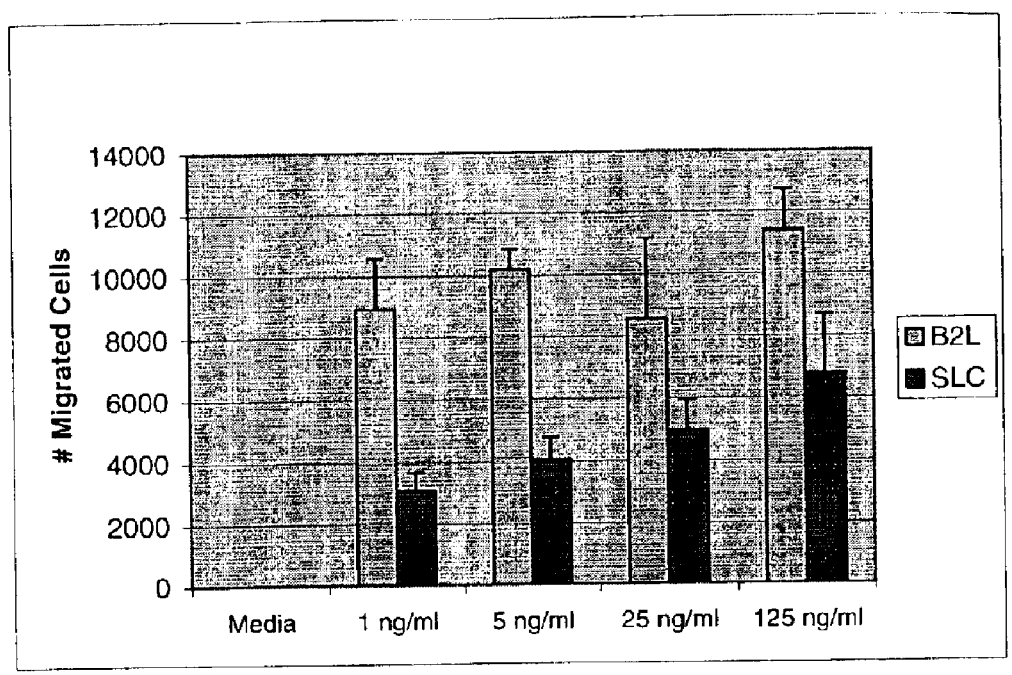
FIG. 2. Chemotactic effect of B2L on murine dendritic cell-enriched cultures of bone marrow cells.

B2L induces distinct immunologic effects. Because it is a foreign protein, it is recognized as an antigen by T and B lymphocytes with antigen receptors specific for B2L. It also activates antigen nonspecific cells including, but not limited to dendritic cells which do not express antigen specific receptors and thereby causing antigen-nonspecific inflammatory responses. It may be desirable to elicit a nonspecific inflammatory response to the B2L protein without a concomitant specific immune response to the protein. Development of an inflammatory response can be determined by evaluating serum or plasma from treated individuals for the presence of proinflammatory cytokines including, but not limited to TNFα, IL-1β, IL-6, and IFNγ. Additionally, development of an inflammatory response can be determined by evaluating peripheral blood mononuclear cells or the tissue at the injection site for increased numbers of monocytes, granulocytes, lymphocytes or neutrophils. Development of a specific humoral immune response to B2L can be determined by evaluating serum or plasma from treated individuals for the presence of antibodies that specifically recognize B2L. Additionally, development of a cell mediated immune response to B2L can be determined by evaluating the selective proliferation of and/or cytokine production by peripheral blood mononuclear cells or isolated lymphocytes in response to in vitro exposure to the B2L protein It may be desirable to immobilize either the B2L protein or the test compound to facilitate separation of bound from unbound forms of one or both of the interactants, as well as to accommodate automation of the assay. Thus, either the B2L or the test compound can be bound to a solid support. Suitable solid supports include, but are not limited to, glass or plastic slides, tissue culture plates, microtiter wells, tubes, silicon chips, or particles such as beads (including, but not limited to, latex, polystyrene, or glass beads). Any method known in the art can be used to attach the B2L protein or the test compound to a solid support, including use of covalent and non-covalent linkages, passive absorption, or pairs of binding moieties attached respectively to the B2L protein or test compound and the solid support. Test compounds are preferably bound to the solid support in an array, so that the location of individual test compounds can be tracked. Binding of a test compound to a B2L can be accomplished in any vessel suitable for containing the reactants. Examples of such vessels include microtiter plates, test tubes, and microcentrifuge tubes.

All patents and patent applications cited in this disclosure are expressly incorporated herein by reference. The above disclosure generally describes the present invention. A more complete understanding can be obtained by reference to the following specific examples, which are provided for purposes of illustration only and are not intended to limit the scope of the invention.

EXAMPLE 1

Chemotaxis of Human Dendritic Cells in Response to B2L

Proteins that are chemotactic for dendritic cells would be useful as single agent therapeutics in cancer patients (Fushimi et al. J. Clin. Invest. 2000. 105:1383; Sharma et al. J Immunol. 2000. 164:4558). *Parapoxvirus ovis* causes dendritic cell recruitment. To determine if the isolated B2L protein of the parent virus exhibited similar chemotactic activity, human peripheral blood mononuclear cells were cultured with GM-CSF and IL-4 to allow differentiation of dendritic cells. After labeling with Calcein-AM dye, $10^5$ cells were loaded into the upper compartment of chemotaxis culture chambers and the indicated concentrations of RANTES chemokine or purified V5His6-tagged, Strep-tagged or untagged B2L protein loaded into the lower compartment. Cell migration through a cell-permeable membrane separating the two compartments was assessed after 2 hr 15 min. The results shown in FIG. 1 confirm published reports that RANTES chemokine causes migration of human dendritic cells. Similarly, dendritic cells migrate in response to V5His6-tagged B2L, albeit to a lesser extent than to RANTES in the experiment shown. Heat inactivation of the protein resulted in loss of chemotactic activity, demonstrating that activity was not a function of trace levels of endotoxin in the preparation (not shown). The chemotactic activity is a function of the B2L protein itself rather than of the V5His6 epitope tag, as demonstrated by comparable activity of the untagged molecule. These results suggest that B2L administered intratumorally, as a single agent would recruit dendritic cells to the site of tumor antigen. This would facilitate uptake of endogenous tumor antigens by the dendritic cells and subsequent induction of a systemic tumor specific immune response.

EXAMPLE 2

Chemotaxis of Murine Dendritic Cells in Response to B2L

Proof of concept studies were designed in murine tumor models. Murine secondary lymphoid chemokine (mSLC) is known to elicit an antitumor immune response when administered intratumorally. The doses needed for this activity have been published. To select a range of doses of V5His6-tagged B2L likely to exhibit antitumor activity in mice, we compared the amount of tagged B2L needed for migration of murine dendritic cells with the amount of mSLC needed. Murine bone marrow cells were cultured with GM-CSF and IL-4 for 5 days to enrich for dendritic cells. After labeling with Calcein-AM dye, $10^5$ cells were loaded into the upper compartment of chemotaxis culture chambers and the indicated concentrations of murine SLC chemokine or purified V5His6-tagged B2L protein into the lower compartment. Cell migration through a cell-permeable membrane separating the two compartments was assessed after 2 hr 15 min. The results shown in FIG. 2 depict a relatively shallow dose response curve for both proteins but indicate that the chemotactic activity of the tagged B2L is at least as potent as that of mSLC and suggested that equivalent doses of both proteins intratumorally might exhibit antitumor activity.

EXAMPLE 3

Local and Systemic Antitumor Activity of Intratumorally Administered B2L

Local antitumor activity had previously been reported for intratumorally administered dendritic cell chemoattractants. Therapeutic application would be severely limited if activity were confined to the accessible tumor. Therefore, therapeutic efficacy of tagged B2L was evaluated in a double-implant model to allow evaluation not only of local efficacy but systemic efficacy as well. B16.F10 murine melanoma cells were implanted both subcutaneously and intravenously, the former providing a tumor accessible to drug administration and the latter leading to development of pulmonary tumor nodules distant to the site of drug administration. Intratumoral administration of V5His6-tagged B2L into the subcutaneous tumor nodule, indicated by the black arrows, began on day 6 when nodules became palpable. As expected, based on published literature, tumor growth measured on day 21 was inhibited by mSLC at both subcutaneous (FIG. 3A) and pulmonary sites (FIG. 3B) by 50% ($p<0.001$) and 39% ($p<0.02$), respectively. Similarly, intratumorally administered tagged B2L inhibited growth of the injected subcutaneous tumor by 55% ($p<0.01$) and the development of pulmonary nodules by 53% ($p<0.01$). These results indicate that tagged B2L exhibits antitumor activity comparable to that of mSLC. Furthermore, administration of tagged B2L resulted in growth inhibition even when administered at a site distant to the tumor. This result is consistent with the possibility that intratumoral administration of tagged B2L led to development of a systemic antitumor immune response.

EXAMPLE 4

Immune Dependence of Local and Systemic Antitumor Activity of Intratumorally Administered B2L To evaluate the potential role of the cell-mediated immunity in the antitumor activity found for tagged B2L, efficacy was compared in normal immunocompetent mice and in mice rendered partially immunodeficient by depletion of T and natural killer (NK) lymphocytes. B16.F10 tumor was implanted both subcutaneously and intravenously. Administration of V5His6-tagged B2L into the subcutaneous tumor nodule, indicated by the black arrows, began on day 6 when nodules became palpable. Immune depletion of T and NK cells was achieved through IP injections of antibodies, indicated by red arrows, to these cell types. Tumor growth measured on day 21 was inhibited at both subcutaneous (FIG. 4A) and pulmonary sites (FIG. 4B) by 68% and 48%% ($p<0.001$), respectively, in immunocompetent mice whereas antitumor activity was not observed in T and NK-depleted littermates. These results indicate that the antitumor activity of intratumorally administered tagged B2L is immune dependent.

EXAMPLE 5

B2L Augments IFNγ Production by Human PBMC

Parapoxvirus ovis is known to exhibit nonspecific immunostimulatory effects in animals when administered systemically. The mechanism underlying this effect is believed to be cytokine mediated. Parapoxvirus ovis has been shown to induce cytokine production from human PBMC. If B2L exhibited similar activity in vitro, one could hypothesize that it would exhibit antitumor activity in vivo when administered systemically. To our knowledge, this has not been tested. To do so, human PBMC collected from 3 donors were cultured with 1 or 100 ng/ml untagged B2L alone (not shown), 100 ng/ml LPS alone or in combination with the indicated concentrations of B2L. Supernatants were collected after 48 hours and assayed by a bead-based ELISA (Luminex) for the presence of IFNγ, a cytokine known to have antitumor activity. B2L alone exhibited no effect on PBMC within the timeframe of the experiment (not shown). LPS alone elicited only modest production of IFNγ. The addition of B2L led to substantial increases in the level of IFNγ produced by from two of the three donors in the experiment shown. In repeated experiments, the increase in IFNγ production ranged between 2 and 7 fold. The activity was a function of the B2L protein itself and not a tag, since untagged B2L was used in these experiments. The ability of B2L to elicit in vitro production of IFNγ raises the possibility that systemic administration of B2L as a single agent might lead to systemic cytokine production and antitumor activity.

EXAMPLE 6

Figure 6:
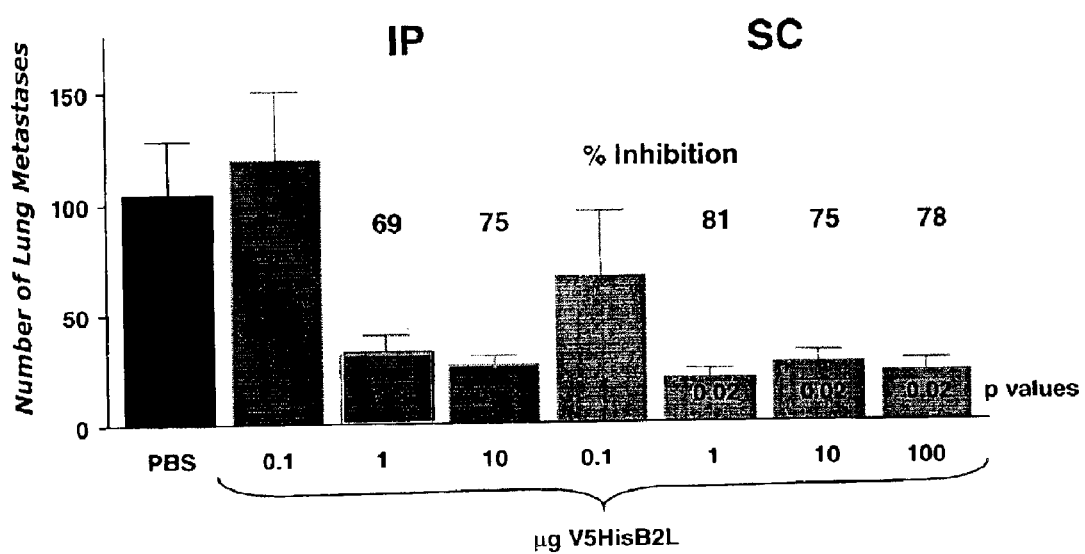
FIG. 6 Subcutaneous and intraperitoneal administration of tagged B2L results in tumor growth inhibition FIG. 7 Subcutaneous administration of untagged B2L results in tumor growth inhibition FIG. 8. Intravenous administration of untagged B2L results in tumor growth inhibition FIG. 9. Systemic administration of B2L results in tumor growth inhibition in multiple tumor models and mouse strains

Subcutaneous and Intraperitoneal Administration of Tagged B2L Results in Tumor Growth Inhibition Due to its additional ability to elicit production of cytokines such as IFNγ which are known to have antitumor activity, one can hypothesize that B2L would exhibit antitumor activity if administered systemically as well. To test this hypothesis, V5His-tagged B2L was administered intraperitoneally (IP) (the $2^{nd}$, $3^{rd}$, and $4^{th}$ bars, numbered from the left—under the heading "IP") or subcutaneously (SC) ($5^{th}$, $6^{th}$, and $7^{th}$ bars, numbered from the left—under the heading "SC") once daily for 5 consecutive days beginning the $6^{th}$ day after intravenous implantation of B16.F10 tumor (see: FIG. 6). The results shown in FIG. 6 demonstrate that a daily dose of 0.1 µg given by either route of administration was ineffective. A daily dose of at least 1 µg, however, led to 70–80% reduction in the number of pulmonary nodules. This was seen with both routes of administration. Daily doses higher than 1 µg offered no greater therapeutic benefit. Combined with the results in FIG. 5, these results support the therapeutic hypothesis that systemic administration of B2L as a single agent would result in tumor growth inhibition in cancer patients.

EXAMPLE 7

Subcutaneous Administration of Untagged B2L Results in Tumor Growth Inhibition

Figure 7:
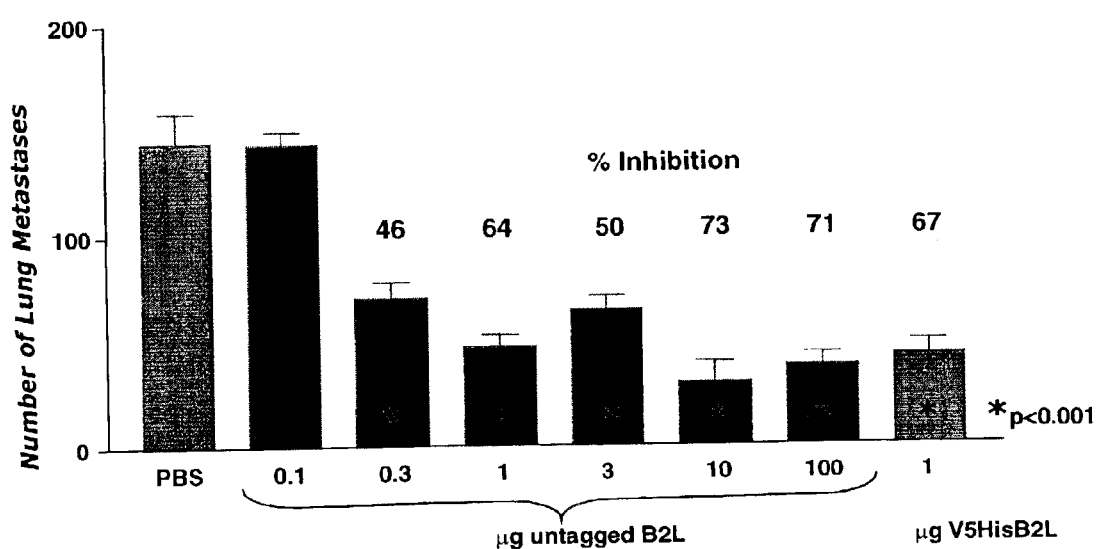
Figure 8:
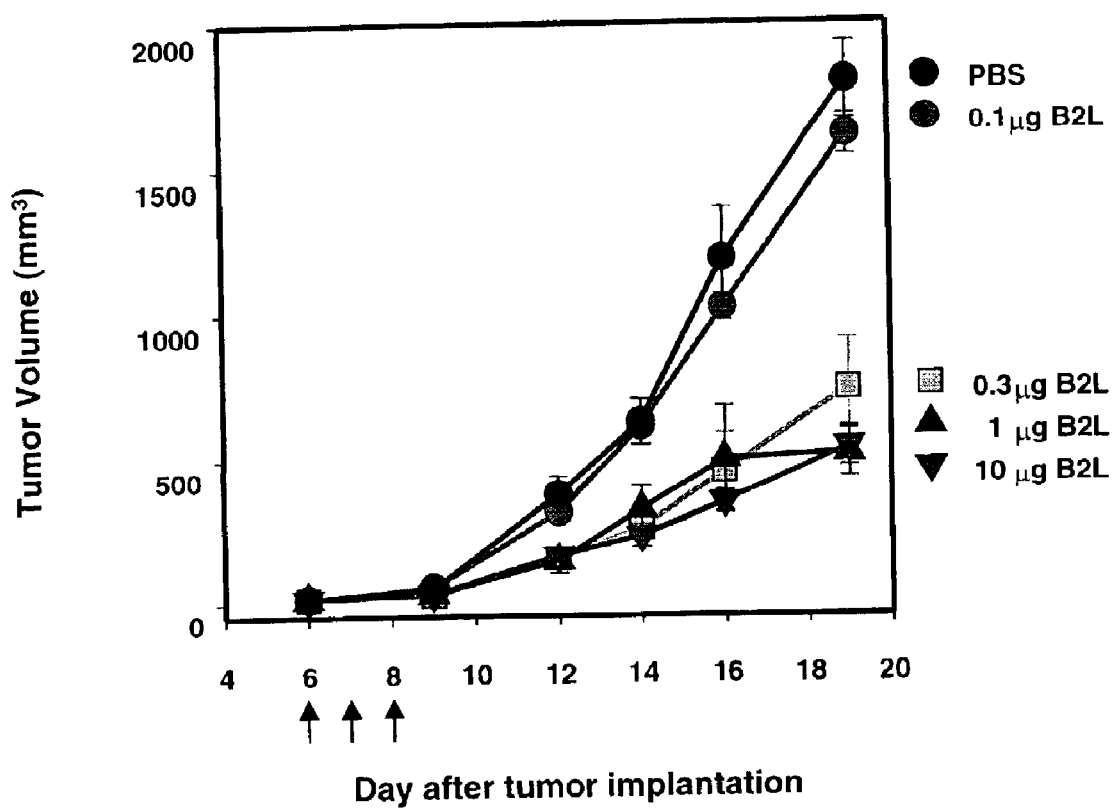

To evaluate the potential contribution of the epitope tag to the antitumor efficacy found, V5His6-tagged (bar at far right side of histogram, below the number 67) or untagged (the six bars labeled "µg untagged B2L") B2L were administered SC once daily for 5 consecutive days beginning the $6^{th}$ day after intravenous implantation of B16.F10 tumor (FIG. 7). As observed previously with tagged B2L, the results shown in FIG. 7 demonstrate that untagged B2L is ineffective when administered at a daily dose of 0.1 µg but reduces the number of pulmonary nodules by 50–70% (p<0.001) when administered at daily doses of at least 1 μg. A daily dose of 0.3 μg demonstrated statistically significant efficacy in the experiment shown. This is not a consistently reproducible finding (not shown), indicating a very steep dose response. These results demonstrate that antitumor efficacy is a function of the B2L protein itself, not the epitope tag.

EXAMPLE 8

Intravenous Administration of Untagged B2L Results in Tumor Growth Inhibition

In a limited number of studies, efficacy of untagged B2L was also evaluated after IV administration once daily for 3 consecutive days beginning the 6$^{th}$ day after SC implantation of B16.F10 tumor. The results shown in FIG. 8 demonstrate that a brief 3-day course of therapy with untagged B2L reduces tumor growth by 60–70% (p<0.05) when administered at a daily dose of at least 0.3 μg but is ineffective when administered at a dose of 0.1 μg.

EXAMPLE 9

Figure 9:
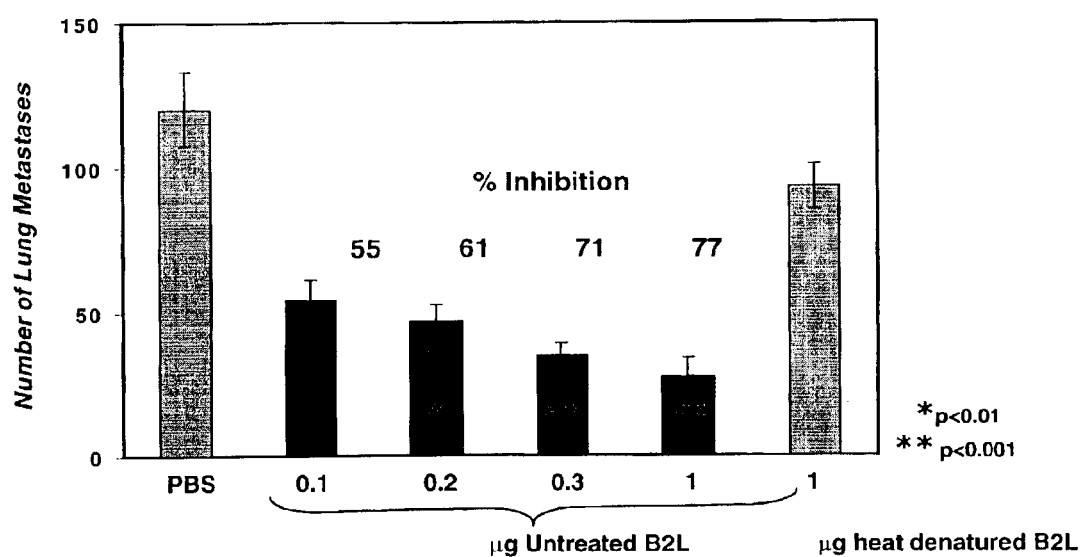

Subcutaneous Administration of B2L Results in Tumor Grown Inhibition in Multiple Tumor Models and Mouse Strains C57BL/6 mice are genetically predisposed to make a Th1 type of immune response, characterized in part by the preferential production of IFNγ. Conversely, BALB/c mice are genetically predisposed to make a Th2 type of immune response, characterized in part by less robust IFNγ responses. The genetic variability of humans also contributes to variability in the types of immune responses they mount. To determine if B2L would exhibit antitumor efficacy in mice of a low IFNγ producing background, untagged B2L was administered SC once daily for 5 consecutive days in BALB/c mice, beginning the 6$^{th}$ day after intravenous implantation of syngeneic CT-26 colon carcinoma cells. The results shown if FIG. 9 (four bars identified as "μg Untreated B2L") demonstrate that a daily dose of 1 μg, the minimal daily dose that consistently exhibits maximal efficacy in C57BL/6 mice bearing B16.F10 tumors, also exhibits robust antitumor activity in BALB/c mice with established CT-26 tumors. These results suggest that B2L will exhibit antitumor activity in animals and humans of immunologically relevant genetic variability. Due to its effect on dendritic cells and IFNγ production, B2L preparations impact the innate immune system. The innate immune system is highly sensitive to endotoxin, a contaminant frequently found in biologic preparations. The preparations of tagged and untagged B2L used typically contained <1 EU/mg of endotoxin (not shown). Nonetheless, B2L was heat denatured, a process which generally inactivates proteins but does not affect endotoxin. The pale blue bar indicates that heat denatured B2L is inactive, indicating that the activity is a function of the B2L protein itself and not due to trace levels of endotoxin.

We claim:

1. A method of treating a patient having a cell proliferative disorder, comprising the step of:

administering to the patient an effective amount of a purified and isolated B2L viral envelope protein of a *Parapox* virus, whereby symptoms of the patient's cell proliferative disorder are ameliorated.

2. The method of claim 1 wherein the B2L protein is administered systemically.

3. The method of claim 1 wherein the B2L protein is injected into a tumor or dysplastic lesion.

4. A method of enhancing an immune response to endogenous antigens associated with a cell proliferative disorder, comprising the step of:

administering to a subject in need thereof an effective amount of a purified and isolated B2L viral envelope protein of a *Parapox* virus, whereby the B2L viral envelope protein enhances the immune response to the endogenous antigens.

* * * * *